(12) United States Patent
Kreisler et al.

(10) Patent No.: US 12,422,576 B2
(45) Date of Patent: Sep. 23, 2025

(54) X-RAY FACILITY AND METHOD FOR OPERATING AN X-RAY FACILITY

(71) Applicant: Siemens Healthineers AG, Forchheim (DE)

(72) Inventors: Björn Kreisler, Hausen (DE); Edgar Göderer, Forchheim (DE); Stefan Wirth, Erlangen (DE)

(73) Assignee: Siemens Healthineers AG, Forchheim (DE)

( * ) Notice: Subject to any disclaimer, the term of this patent is extended or adjusted under 35 U.S.C. 154(b) by 224 days.

(21) Appl. No.: 18/234,578

(22) Filed: Aug. 16, 2023

(65) Prior Publication Data

US 2024/0061134 A1   Feb. 22, 2024

(30) Foreign Application Priority Data

Aug. 19, 2022   (EP) .................................... 22191231

(51) Int. Cl.
   *G01T 1/24*   (2006.01)
   *A61B 6/00*   (2006.01)
(52) U.S. Cl.
   CPC ................. *G01T 1/244* (2013.01); *A61B 6/00* (2013.01); *A61B 6/5282* (2013.01)
(58) Field of Classification Search
   CPC .......... G01T 1/244; A61B 6/00; A61B 6/5282
   See application file for complete search history.

(56) References Cited

U.S. PATENT DOCUMENTS

| | | | |
|---|---|---|---|
| 5,444,752 A * | 8/1995 | Dobbs ...................... | G21K 5/04 378/19 |
| 6,037,595 A | 3/2000 | Lingren | |
| 2003/0132391 A1 | 7/2003 | Agano | |
| 2017/0254907 A1 * | 9/2017 | Ergler ....................... | G01T 1/18 |
| 2018/0199899 A1 * | 7/2018 | Ergler .................. | A61B 6/4208 |

FOREIGN PATENT DOCUMENTS

JP        2003209665 A      7/2003

* cited by examiner

*Primary Examiner* — Hugh Maupin
(74) *Attorney, Agent, or Firm* — Lempia Summerfield Katz LLC (57) ABSTRACT

An X-ray imager having an X-ray source, a semiconductor detector, and a processor. On a rear side of the semiconductor detector facing away from the front side, in each of a plurality of imaging regions of the semiconductor detector, at least one imaging electrode is arranged and a plurality of detectors each contact at least one of the imaging electrodes in order to acquire first measurement values relating to X-ray signals of the imaging electrodes. The processor is configured to establish an image dataset dependent upon the first measurement values. At least one additional electrode is arranged on the rear side of the semiconductor detector outside the imaging regions. At least one current sensor contacts the additional electrode or at least one of the additional electrodes in each case to acquire the current flow by way of the second measurement values relating to the at least one additional electrode.

17 Claims, 3 Drawing Sheets

X-RAY FACILITY AND METHOD FOR OPERATING AN X-RAY FACILITY

RELATED APPLICATION

This application claims the benefit of EP 22191231.4, filed on Aug. 19, 2022, which is hereby incorporated by reference in its entirety.

FIELD

The present disclosure relates to an X-ray facility (X-ray imaging or scanner) with an X-ray source, a semiconductor detector, and a processing facility (processor). On the rear side of the semiconductor detector facing away from the front side, in each of a plurality of imaging regions of the semiconductor detector, at least one imaging electrode is arranged and a plurality of imaging detectors (pixels or sensors) of the X-ray facility each contact at least one of the imaging electrodes in order to acquire first measurement values relating to X-ray signals of the imaging electrodes. The processing facility is designed to establish an image dataset dependent upon the first measurement values. At least one additional electrode is arranged on the rear side of the semiconductor detector outside the imaging regions. A method for operating an X-ray facility is provided.

BACKGROUND

The use of semiconductor detectors, in particular, single photon detectors in X-ray facilities, for example, in computed tomographs is per se known. In single photon detection, a bias voltage is applied to the semiconductor material of the semiconductor detector, for which typically a full surface electrode on the front side is used. On the rear side, separate electrodes are provided for individual pixels of the semiconductor detector. If an electron-hole pair is created in the semiconductor material by an X-ray photon, then by reason of the bias voltage, a charge cascade is triggered and the current spike resulting therefrom can be acquired in that currents flowing out via the imaging electrode, that is, the electrode applied to the detector rear side for each pixel, is acquired via a respective imaging detector. The number of detected current spikes herein denotes, provided X-ray intensities are not too high, the number of acquired X-ray photons, while the height of the current spike correlates to the photon energy of the respective photon and can therefore be used for energy-resolved imaging.

To achieve a separation of the detection events for the individual image points, firstly an anti-scatter grid is typically used and is arranged in front of the semiconductor detector. The anti-scatter grid can be made entirely of an X-ray absorbent material or portions of X-ray absorbent material can be connected to one another by less X-ray absorbent spacers, made for example of cellulose or aluminum. The regions of the semiconductor material screened by the X-ray absorbent material can also be designated a guard ring.

For improved image point separation, influence is often exerted in a targeted manner on the field distribution of these guard rings. This can also be achieved with locally different dopings of the semiconductor material. Preferably, however, in the region opposite the X-ray absorbent material on the rear side of the semiconductor detector, additional electrodes are provided that can be connected to a defined potential in order to influence the field distribution in the guard ring region.

The measured currents for the individual detector pixels depend heavily upon local properties of the semiconductor. Thus, a temperature increase in the semiconductor leads to higher levels of dark current for the heated detector pixels and local doping differences which can also result, for example, from the X-ray irradiation can also influence the measured current flows. To achieve a high imaging quality, the local properties of the semiconductor must therefore be known as accurately as possible and/or an attempt must be made to keep the state of the semiconductor as stable as possible during the measurement.

For this purpose previously, firstly, a tempering of the semiconductor detector has been used and, secondly, it has been possible to make dark current measurements for the individual detector pixels. Since, however, typical dark current measurements must be carried out outside the normal measuring operation, for example with the X-ray tube switched off and/or after the closing of a shutter, changes to the semiconductor properties during the measurement, for example, a local heating due to bias currents flowing during the measurement, thus cannot be taken into account and therefore lead to errors in the imaging.

In known approaches for tempering the detector, the heating of the detector also takes place on the basis of temperature measurements and therefore via a relatively sluggish control loop. This can also impair imaging.

SUMMARY AND DESCRIPTION

It is therefore an object further to improve an imaging process by way of an X-ray facility. The improved imaging process can involve, for example, the acquisition of a single X-ray image or the acquisition of a plurality of X-ray projections, for example, in the context of computed tomography.

The object is achieved, according to an embodiment, in that at least one current sensor contacts the additional electrode or at least one of the additional electrodes in each case in order to acquire the current flow by way of the second measurement values relating to the at least one additional electrode.

The second measurement values can serve to describe and/or estimate a state of the semiconductor sensor. For example, a temperature of the semiconductor sensor, an ageing state, a quality measure, for example, in relation to the doping properties of the semiconductor material, or suchlike can be described by way of the second measurement values and/or established on the basis thereof.

In particular, the first measurement values describe the spatial distribution of the X-ray radiation absorbed by way of the semiconductor detector and thus, in particular directly, a mapping of the absorbed X-ray radiation and/or of the transirradiated object which is to be described by the image dataset. The image dataset can thus be established exclusively dependent upon the first measurement values, although it is also possible to carry out the establishing of the image dataset additionally in dependence upon the second image data and/or on the basis of the second measurement values, to correct a preliminary image dataset which depends exclusively upon the first measurement values, in order to correct influences of the sensor state upon the imaging.

Expressed differently, in particular, image data can be acquired exclusively in the imaging regions, that is, data which relates to the spatial distribution of the X-ray absorption. The region and/or regions in which the at least one additional sensor is arranged might, in particular, not be used and/or not be suitable for acquiring image data which relates to the distribution of the absorbed X-ray radiation, e.g., due to a screening by, for example, an anti-scatter grid, a collimator or suchlike or on the basis of doping properties of the semiconductor material of the semiconductor detector, and/or might not be used for such an acquisition.

X-ray signals can be, in particular, those signals, for example charge densities present at the electrode and/or currents flowing through it, which have been caused by the absorption of X-ray quanta in the imaging region associated with the respective imaging electrode. The first measurement values can relate, for example, to the frequency and/or the number and/or the height of acquired current spikes and/or in general at least one property of a temporal variation of the current through the imaging electrode, but also, for example, to potential measurements or suchlike.

By way of additional acquisition of the second measurement values, signals, for example currents, are captured which flow through the semiconductor material outside the imaging regions, for example, in shading regions of the semiconductor detector and/or within the guard ring structures. Since these regions are at least largely shielded against X-ray photons from the X-ray source, the currents measured by the second measurement values can be regarded as a type of dark current. In comparison with typical dark current measurements, however, the advantage is achieved that the measurement is possible during the normal measuring process for imaging and thus, for example an influence of a local heating of the X-ray detector by way of incident X-ray radiation can also be taken into account.

In particular, with shared evaluation of the first and second measurement values and using sufficiently many additional electrodes, for example, using an additional electrode between each pair of imaging electrodes, by evaluating the first and second measurement values, the movement of the charge cloud triggered by a respective X-ray photon in the semiconductor material can be recognized and analyzed more accurately, so that for example, additional information regarding the interactions between image points can be established and taken into account in the establishment of the image dataset.

Since, therefore, the currents flowing in the semiconductor material are more accurately known by reason of the evaluation of the second measurement values, for example, the local heating of the semiconductor material by such currents can be predicted with good accuracy, so that for example, it is possible not to carry out the heating of the semiconductor material for tempering the semiconductor detector or at least not exclusively on the basis of an acquired temperature, but rather to predict future temperatures on the basis merely of current flows and thus at least largely to prevent the above-described sluggishness of the temperature stabilization.

As described, the processing facility (processor) can be designed to control at least one component of the X-ray facility (X-ray imager) dependent upon the second measurement values. Preferably, the processing facility is designed, dependent upon the second measurement values, to control a heater for heating the semiconductor detector as the component or one of the components of the X-ray facility.

Additionally, or alternatively, by monitoring the second measurement values, local material changes, for example, higher dark current levels on the basis of the local temperature or on the basis of local defects in the semiconductor can already be recognized during the measurement and therefore taken into account during the evaluation of the first measurement values and/or in the establishment of the image dataset. In a simple example, it can be assumed that the current via the additional electrodes is at least approximately proportional to the dark current if, aside from the irradiation of the X-ray radiation, this has been established under identical conditions. Thus, per se known algorithms for dark current correction in the X-ray facility can, however, be parameterized and/or at least corrected on the basis of the second measurement values in order firstly to be able to take account of changes in the local state of the semiconductor material occurring in the context of the measurement data acquisition and/or in preceding measurements without dark current measurements lying therebetween. The resulting improved dark current correction can enable, for example, temporally closely occurring X-ray detections at the same image point to be better separated.

The acquisition of the second measurement values can also contribute to estimating the overall intensity of the X-ray radiation radiated onto the semiconductor detector with high accuracy, such that it is possible, for example, dependent upon the captured overall intensity, to change between the different evaluating algorithms for generating the image dataset or suchlike.

As described above, the processing facility can advantageously be designed to establish the image dataset additionally dependent upon the second measurement values.

Apart from the control, as described, of a heating of the semiconductor detector and/or taking account of the second measurement values during the image data evaluation, additionally or alternatively, other components of the X-ray facility can also be controlled dependent upon the second measurement values. For example, a collimator setting or a tube voltage can be adapted in order, for example, in the case of very high overall intensities, to reduce the X-ray intensity incident upon the detector. At high X-ray intensities, it can also be suitable, for example, to reduce a bias voltage between a bias electrode at the front side of the semiconductor detector and the imaging electrodes to enable a quicker decay of the current spikes and, therefore, an improved separation of X-ray photons incident shortly after one another.

The X-ray facility can include an anti-scatter grid arranged between the X-ray source and a front side of the semiconductor detector facing toward the X-ray source. At least one shading region of the semiconductor detector is screened from the X-ray source by an X-ray absorbent material of the anti-scatter grid. In each case, the at least one additional electrode is arranged at least partially in the shading region or at least one of the shading regions.

For example, pairs of imaging regions can each be separated from one another by the shading region or at least one of the shading regions. It is herein possible that an acquisition of second measurement values takes place for additional electrodes between all the imaging regions. However, it is also possible that no additional electrodes are present between some of the imaging regions and/or that electrodes are in fact present there and are held at a predetermined potential as in typical semiconductor detectors in order to form a guard ring, but that no current measurement takes place for these electrodes.

The respective additional electrode can extend parallel to a strut of the anti-scatter grid, wherein the additional electrode can be configured, in particular, to be somewhat wider than this strut, for example by a factor of 2 or 5 or 10. A bias electrode arranged on the front side of the semiconductor detector can be designed to be continuous, but can also be formed by way of a plurality of separate electrodes. The anti-scatter grid can consist exclusively of the X-ray absorbent material and can be formed, for example, by a tungsten or lead lattice. It is also possible, however, that X-ray transparent material, for example, cellulose or aluminum is arranged in intermediate regions between portions of X-ray absorbent material.

The processing facility of the X-ray facility can be arranged, for example, in a housing of the X-ray facility, but also as separate components, for example, as workplace computers or servers. It is also possible that the processing facility is implemented as a decentralized system, for example, as a cloud solution.

The imaging electrodes and the at least one additional electrode can each be connected by way of at least one contact (electrical connector) to a connecting electrode of an integrated circuit, which implements the imager. Correspondingly solutions with which, in particular, an application-specific integrated circuit (ASIC) is used as the integrated circuit are per se known for common semiconductor detectors for X-ray facilities in which no current measurement takes place for the additional electrodes. The additional electrodes for current measurement contact via the integrated circuit.

The contact can be, in particular, a rigid contact, for example, solder beads and/or metal beads in general, which can be melted on for contacting.

Within the integrated circuit, a digital-analog conversion of the detected currents and/or the measurement values relating to these currents can take place, in particular directly, so that, for example, a digital communication between the integrated circuit and a processing facility configured separately therefrom can be sufficient.

The integrated circuit can additionally implement the current sensor. Thus, the current measurement can take place in the integrated circuit itself and, in particular, the second measurement values can also be digitized directly.

Alternatively, it would also be possible to feed the current to be measured from the additional electrodes via the integrated circuit, but there to provide for each of the current sensors an additional output of the integrated circuit via which the current can be fed to each separately configured current sensor. Therefore, the current sensor can be configured separate from the integrated circuit, wherein the integrated circuit has a circuit portion which serves to feed the current to be measured from each additional electrode to the respective current sensor.

Since integrated circuits for processing signals from semiconductor detectors in X-ray facilities are often already used to hold electrodes in the shading region at a defined potential, therefore only a relatively slight modification to such known integrated circuits is required, such that the X-ray facility according to one embodiment can be implemented with little effort.

The additional electrode or at least one of the additional electrodes can be connected, via at least two contacts (connectors) spaced apart from one another, to one or each to one connecting electrode of the integrated circuit. By this, firstly, the resistance resulting from this connection is reduced, which can be advantageous since, as explained below, the additional electrodes should preferably be held as exactly as possible at a predetermined potential, despite the current measurement taking place. At the same time, by using a plurality of contacts, it can be achieved that individual defective connections do not, or at least only insignificantly, impair the function of the semiconductor detector, so that a higher yield in the production of the detectors and a longer detector lifespan can be achieved. The use of a plurality of contacts can also be advantageous if relatively large-area additional electrodes are to be used since, by this, local potential differences at the additional electrode can be minimized.

As described above, the processing facility can be designed to control a heater for heating the semiconductor detector as the component or one of the components of the X-ray facility, dependent upon the second measurement values. As described above, the regulation of the heating power of such a heater is particularly relevant in order to achieve the most constant possible operating conditions of the X-ray detector. By taking account of the second measurement values, future temperature changes due to current flows in the semiconductor detector can be predicted and thus regulation delays can be prevented and/or at least reduced.

The heater can serve for even heating of the semiconductor detector or for heating individual segments of the semiconductor detector. If individual segments of the semiconductor detector are heated independently of one another, it is particularly advantageous if, for each of the segments, at least one separate current sensor is used in order to acquire a current via at least one additional electrode there in order to establish local current flows in the individual segments and to take account thereof in the heating.

The additional electrode or, in each case, at least one of the additional electrodes can be designed as a straight strip and/or as a strip surrounding a, in particular rectangular, imaging region and/or cruciform.

A straight strip can extend, in particular, parallel to a strut of the anti-scatter grid. Particularly preferably, such a strip extends over a length between two further struts extending perpendicularly thereto of the anti-scatter grid so that it substantially covers a lateral boundary of an imaging region. Alternatively, it is however also possible to use significantly shorter strips to measure substantially punctiform local currents. By using strip electrodes and/or substantially punctiform additional electrodes, in particular, currents can be measured at different boundary surfaces which delimit an imaging region in relation to a respective further imaging region, whereby, for example, currents in a detector pixel can be estimated more accurately on the basis of an X-ray detection in an adjacent detector pixel.

However, the use of a strip surrounding the imaging region can be advantageous to be able to estimate a local condition in precisely this imaging region particularly accurately.

The use of cruciform additional electrodes can be advantageous to estimate with a single additional electrode, for example, local states in four adjoining imaging regions. This can be advantageous, for example, if relatively few additional electrodes are to be used.

The additional electrode and the imaging electrodes can be electrically connected to one another or to a common reference potential such that the potential on the imaging electrodes and the potential on the at least one additional electrode differ from one another during operation of the X-ray facility by not more than 1 Volt or not more than 200 mV.

For this purpose, the respective additional electrode and the imaging electrodes can, for example, be connected in particular via the respective current sensor and/or the respective imager or detector, to a reference point lying during operation of the X-ray facility at a reference potential, such that the resistance between a bias electrode arranged at the front side of the semiconductor detector and the respective additional electrode and/or imaging electrode is larger by a factor of 10 or 100 than the resistance between this additional and/or imaging electrode and the reference point. The reference point can be, in particular, a connection of the integrated circuit which implements the current measurement.

By way of the low-ohmic connection to the reference point, it can be achieved that the additional electrode can be held substantially at the reference potential. In particular, deviations of less than 0.1 V from the reference potential can be realized and thus a similarly exact specification of the reference potential as is usual in semiconductor detectors with electrodes in the shading region, for which no current measurement takes place.

The connection to the reference point can take place, in particular, low-ohmically via the current sensor.

A plurality of coherent subregions of the semiconductor detector, each of which includes at least one of the imaging electrodes, can each be associated with at least one of the current sensors which contacts at least one of the additional electrodes which is arranged in this subregion, to acquire the current flow by way of second measurement values relating to this additional electrode. Thus, current flows can be established in a spatially resolved manner for a plurality of subregions in a plurality of shading regions in order, for example, to be able to recognize and take account of a local heating of the semiconductor detector and/or local material changes.

In addition to the X-ray facility, a method is provided. The method is for operating an X-ray facility which includes an X-ray source and a semiconductor detector, wherein on the rear side of the semiconductor detector facing away from the front side, at least one imaging electrode is arranged in each of a plurality of imaging regions of the semiconductor detector which lie outside of the shading region, wherein at least one additional electrode is arranged on the rear side of the semiconductor detector outside the imaging regions. The method includes the steps:

acquiring first measurement values relating to X-ray signals of the imaging electrodes, acquiring second measurement values relating to the current flow through the at least one additional electrode, and establishing an image dataset dependent upon the first measurement values.

The method according to an embodiment can be further developed with the features described for the X-ray facility by way of the advantages mentioned there, and vice versa.

If one component of the X-ray facility is to be controlled, the acquisition of the first measurement values can take place, in particular, after the acquisition of the second measurement values and the control of the components. For example, the second measurement values can each be acquired during a preceding X-ray recording, for example, in the case of a computed tomography, during a previously acquired projection recording.

Additionally, or alternatively, it is possible, even during a single image acquisition and/or during a continuous image acquisition, in particular with a low intensity, to adapt the actuation of the components of the X-ray facility dynamically dependent upon the second measurement values.

BRIEF DESCRIPTION OF THE DRAWINGS

Further advantages and details of the invention are disclosed by the following exemplary embodiments and the accompanying drawings. In the drawings, schematically.

DETAILED DESCRIPTION

Figure 1:
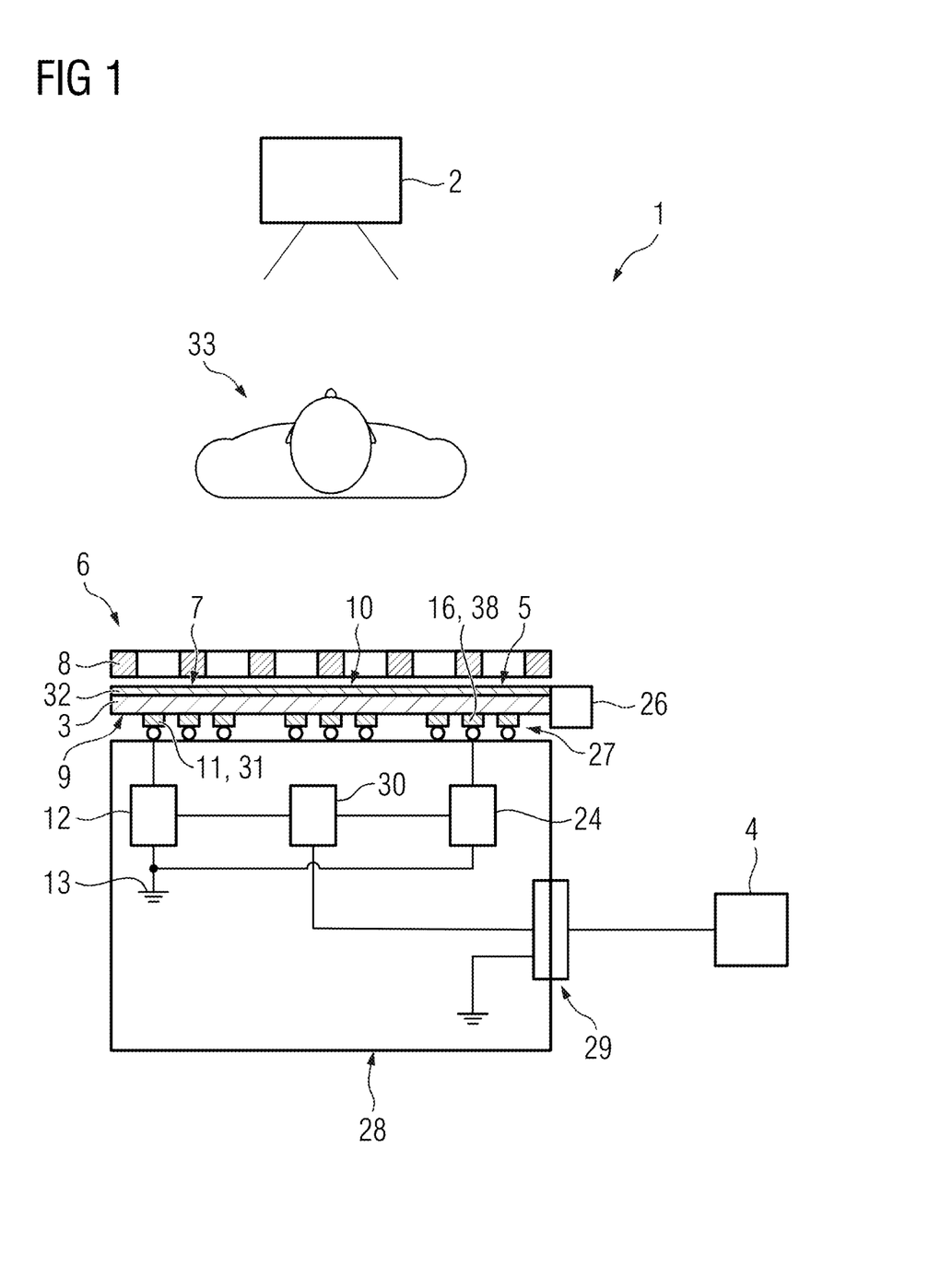
FIG. 1 shows an exemplary embodiment of an X-ray facility.

FIG. 1 shows schematically an X-ray facility (imager or scanner) 1 with an X-ray source 2 and a semiconductor detector 3, by way of which, in the example, an image dataset relating to an examination object 33, e.g., a patient, is to be acquired. The X-ray facility 1 can be, for example, a computed tomography system or an apparatus for recording individual two-dimensional X-ray images.

For clearer representation of the features of relevance, the size relationships between the different components are represented significantly distorted in FIG. 1. In particular, the semiconductor detector 3, the integrated circuit 28 connected thereto, and the anti-scatter grid 6 arranged between the semiconductor detector 3 and the X-ray source 2 are represented significantly enlarged as compared with the examination object 33 and/or the X-ray source 2. For the sake of clarity, a semiconductor detector 3 is also shown with relatively few imaging regions 10 and/or pixels, although in real semiconductor detectors, several hundred imaging regions per row can be implemented.

In the X-ray facility 1, a per se known single photon detection is utilized. Herein, a bias voltage is applied to the semiconductor material of the semiconductor detector 3 in that a bias electrode 32 which, in the example, is continuous on the front side 5 of the semiconductor detector 3 has a bias voltage applied to it and the imaging electrodes 11 arranged on the rear side in the imaging regions 10 are coupled via imaging means (circuit, sensor, or detector) 12 to a reference potential 13. By way of a suitable choice of the bias voltage, on creation of an electron-hole pair in the semiconductor material, a charge cascade results which can be acquired as a voltage pulse via first measurement values of the imaging means 12.

For better separation of the image pixels, arranged between the semiconductor detector 3 and the X-ray source 2 in the example is an anti-scatter grid 6, the X-ray absorbent material 8 of which screens the shading regions 7 of the semiconductor detector 3 lying behind the struts of the anti-scatter grid 6. It is herein known to provide additional electrodes 16 on the rear side 9 of the semiconductor detector 3 in these shading regions 7 and/or generally outside the imaging regions 10, a reference potential 13 being applied to said additional electrodes 16.

However, in contrast to the usual X-ray facilities, in the X-ray facility shown in FIG. 1, at least one current sensor 24 is used which contacts the at least one of the additional electrodes 16 to acquire the current flow through the contacted additional electrode 16 and/or to acquire the second measurement values relating to the contacted additional electrodes 16.

As previously described in the general part, by way of current measurement in the shading regions 7, firstly, a type of dark current measurement can take place even during the measurement itself. Secondly, in particular with locally resolved acquisition of second measurement values by way of using separate current sensors 24 for the additional electrodes arranged in a distributed manner as shown in FIG. 1, a movement of charge clouds in the semiconductor material can be estimated more accurately. By this, local changes in the semiconductor material can be recognized and/or temperature changes due to currents flowing in the semiconductor material can be predicted and thus the actual and future state of the semiconductor detector can be determined more accurately.

This can be used, firstly, to control a component 26 of the X-ray facility, wherein in the example a merely schematically represented heater is controlled for heating the semiconductor detector 3. A corresponding heater is controlled in commonly used X-ray facilities on the basis of a measured semiconductor detector temperature, as a result of which regulating delays can arise. The more accurate acquisition of current flows in the semiconductor detector 3 with the aid of the second measurement values, however, makes it possible in the measuring facility described to estimate a future heating of the semiconductor material before it takes place so that the heater and/or the component 26 can be actuated with a significantly shorter delay or even delay-free in order, for example, in the case of strong current flows in the semiconductor material 3, to reduce the externally fed heating power in order to compensate for a heating of the semiconductor material by way of the internal current flows.

Alternatively, the second measurement values can be used to establish an image dataset that is to be determined dependent upon the first and the second measurement values, that is the measurement values relating to imaging electrodes and relating to additional electrodes. In particular, the second measurement values and thus the current flows in the shading region 7 that are established can be made use of to replace or correct a per se known dark current measurement with an inactive X-ray source 2. Therefore, per se known approaches to dark current subtraction in the context of the image data processing can now additionally take account of the second measurement values in order, for example, to recognize changes to a dark current by way of a local heating during ongoing operation during the measurement and compensate for it during the image data processing.

The establishing of the first measurement values and thus the acquisition of the imaging current spikes and the establishing of the second measurement values is implemented in the example by way of an integrated circuit 28, for example, an application-specific integrated circuit, each of the connecting electrodes of which (not shown) is connected via a contact means (contact or connector) 27, for example, a solder and/or metal bead, to the imaging electrodes 11 and the additional electrodes 16. In the context of the production, for example, the integrated circuit 28 with the contact means 27 formed thereon can be placed on the semiconductor detector 3 and connected thereto both electrically and mechanically by way of melting of the contact means 27.

The first and second measurement values can be acquired digitally by way of the imaging means and/or current sensors and transmitted via a communication interface 30, for example a serial interface, to the processing facility 4. The connection takes place in the example via the plug-in connection 29, via which the reference potential 13 can also be provided. Herein, the connection of the additional electrodes 16, via the contact means 27 and the respective current sensor 24, to the reference potential 13 and the connection of the imaging electrodes 11 via the contact means 27 and the respective imaging means (sensor) 24 to the reference potential 13 are sufficiently low-ohmic and/or at least similarly resistive such that the potential 38 at the additional electrode 16 deviates by not more than 0.1 V from the potential 31 at the imaging electrodes. For this purpose, the resistance of this low-ohmic connection can be at least a factor of 100 lower than the resistance brought about by the semiconductor material 3 between the additional electrode 16 and the bias electrode 32.

For resistance reduction and/or to improve the error tolerance in the production of the semiconductor detector and/or to increase its lifespan, it can be suitable to connect the respective additional electrodes 16 individually via a plurality of the mutually spaced contact means 27. Herein, for each of the contact means 27, a separate connecting electrode of the integrated circuit 28 can be provided or the different contact means 27 can contact the same connecting electrode.

Figure 2:
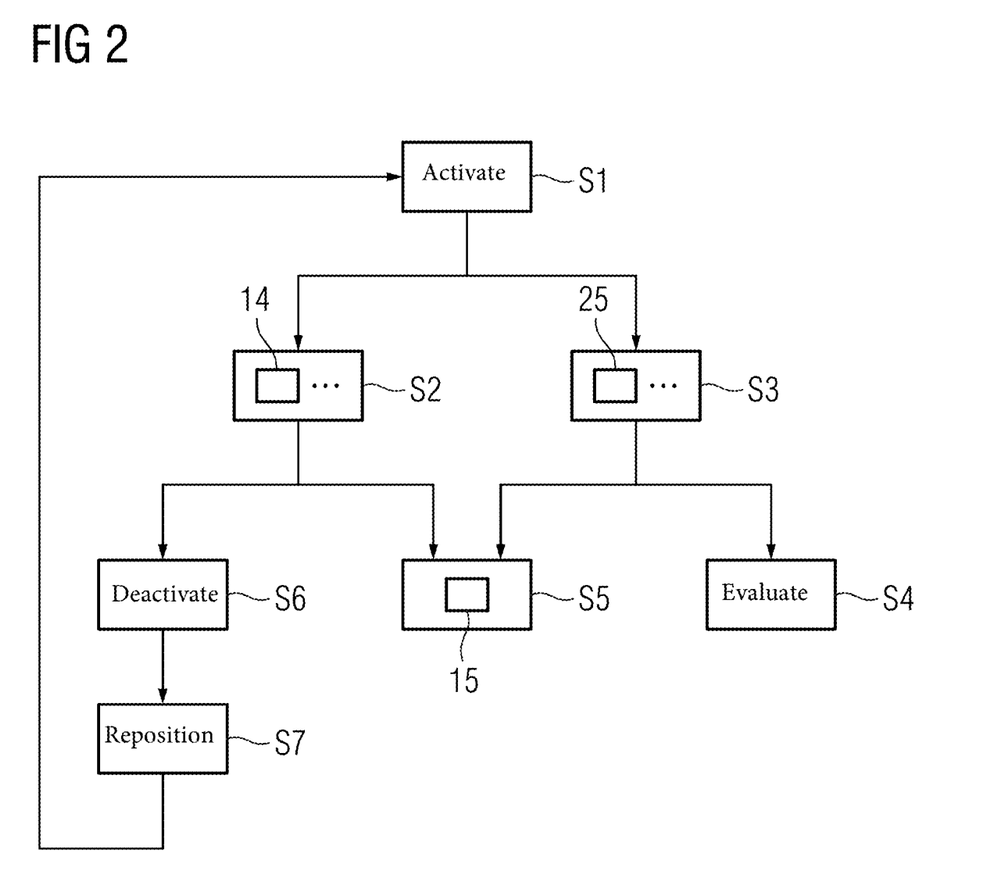
FIG. 2 shows a flow diagram of an exemplary embodiment of the method.

FIG. 2 shows a flow diagram of a possible method for operating the X-ray facility 1 shown in FIG. 1. Herein, in step S1, the X-ray source 2 is activated, for example by applying a current to an X-ray tube and/or by opening a shutter.

In step S2, via the imaging means (sensors or detectors) 12, first measurement values 14 are acquired which each relate to X-ray signals of at least one imaging electrode 11 connected to the respective imaging means 12. Herein, in particular for each image point of the image dataset 15 established, at least one imaging means 12 is provided in order to acquire X-ray intensities in the imaging region 10 associated with this image point of the semiconductor detector 3. For the sake of clarity, only one of these imaging means 12 is shown in FIG. 1.

In step S3, in particular in parallel with step S2, currents are each acquired via at least one current sensor 24 via at least one additional electrode 16 in each case, as the second measurement values 25. Preferably, this measurement also takes place spatially resolved, so that a plurality of current sensors 24 can be used, of which, for the sake of clarity, only one is shown in FIG. 1.

In step S4, the second measurement values 25 are evaluated to control the component 26, in the example, a heating facility for the semiconductor detector 3. This and a possible control of other relevant components has already been described above.

Whereas it is possible, in principle, to carry out a corresponding actuation directly, it can be suitable firstly to wait for the end of a current imaging process and to carry out a corresponding actuation of the components no sooner than in a prepared step for a subsequent image recording, for example, before the recording of a further projection in the context of a computed tomography.

In step S5, an image dataset 15 is established. In the example, this establishing takes place both dependent upon the first measurement values 14 and also dependent upon the second measurement values 25. For example, on the basis of the second measurement values 25, dark currents can be estimated for a plurality of portions of the semiconductor detector 3, which can be taken into account in the context of a dark current correction in the processing of the first measurement values 14 which otherwise can take place in the usual manner.

Although in the example shown, both the actuation of a component 26 takes place dependent upon the second measurement values 25 in step S4 and also the taking into account of the second measurement values 25 during the establishing of the image dataset 15, embodiments of the method described are possible in which the second measurement values 25 are used only in one of the two described ways.

In step S6, the X-ray source 2 is deactivated after acquisition of the first and second measurement values 14, 25 and the acquisition of the current X-ray image and/or a current projection in the acquisition of computed tomography data is thus ended. In step S7, for example, a repositioning of the X-ray source 2 and of the semiconductor detector 3 and of the components connected thereto can now take place in order to map the examination object 33, for example, from a different point of view, following which the method from step S1 can be repeated.

Figure 3:
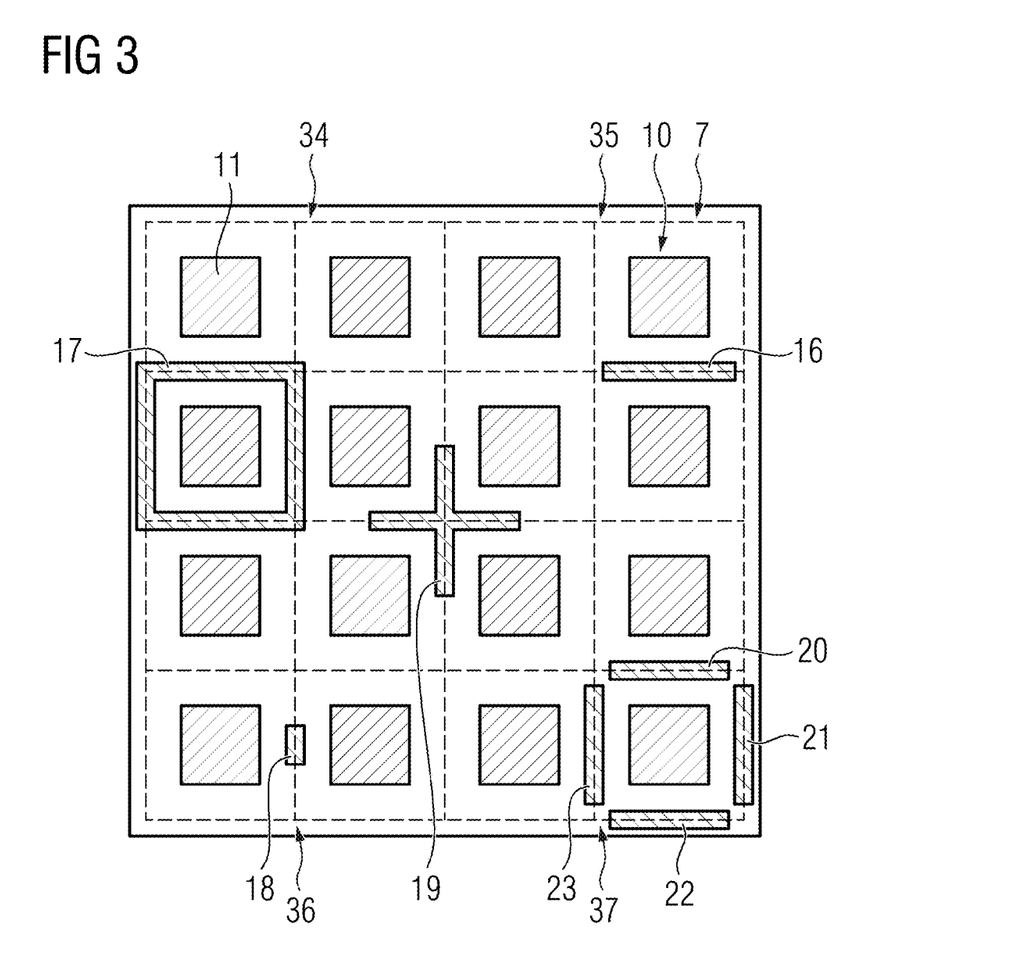
FIG. 3 shows an exemplary arrangement of imaging electrodes and additional electrodes on a semiconductor sensor in a further exemplary embodiment of an X-ray facility.

FIG. 3 shows a plan view onto the rear side of a semiconductor detector which can be used in the X-ray facility described above. For reasons of clarity, a semiconductor detector with very few imaging regions 10 is again shown, in the example with sixteen imaging regions 10. The imaging regions 10 are separated from one another by the grid-shaped shading region 7 which is defined by the shape of the struts of the anti-scatter grid (not shown).

An imaging electrode 11 is arranged in each of the imaging regions 10. By measuring the current flowing through each imaging electrode 11, in particular by counting current spikes, an X-ray intensity incident in the respective imaging region 10 can be established, so that a current spike count per unit time can be used, for example, as an image value of an image point associated with the imaging region 10.

In the example shown, a plurality of differently formed additional electrodes 16-23 are used, for each of which, for example, separately an acquisition of second measurement values can take place via an associated current sensor. The use of very many different additional electrode forms on a single semiconductor detector is undertaken primarily for illustration purposes. In real semiconductor detectors, typically just one or two different forms of the additional electrodes 16-23 are used, wherein however in some cases it can be advantageous to use more different forms.

The additional electrode 16 is strip-shaped and extends parallel to a strut of the anti-scatter grid between two imaging regions 10. A design of this type can be advantageous, for example, the better to recognize current flows between imaging regions 10, and thus mutual influencing of image points, and potentially to correct it.

The additional electrode 17 completely surrounds an imaging region 10 in strip-like manner. This can be advantageous to acquire local properties of the surrounded imaging region 10 robustly and with little effort, for example to take account of a dark current that is to be expected there and to take it into account, for example, in the image data evaluation and/or to use it for adapting a heating control system.

As shown for the additional electrode 18, a current acquisition can also take place just for a short portion of the intermediate region between two imaging regions 10 in order, for example, by using a plurality of such additional electrodes to achieve a greater spatial resolution for the establishment of the second measurement values.

The cruciform shape of the additional electrode 19 enables local properties in all four adjoining imaging regions 10 to be recognized and taken into account with a high level of accuracy by way of a single electrode.

The additional electrodes 20-23 correspond in their shape to the additional electrode 16 but are grouped surrounding one imaging region 10. If all four additional electrodes 20-23 are contacted by a common current sensor, a similar measurement result comes about as for the use of the additional electrode 17.

If, however, separate second measurement values are established for the four additional electrodes 20-23, then as described in relation to the additional electrode 16, current flows between adjoining imaging regions 10 can be analyzed and also the properties in the imaging region 10 can be estimated particularly accurately, as described in relation to the additional electrode 17. However, it can be disadvantageous in such an embodiment that relatively many contacts to an integrated circuit are required if such an arrangement of additional electrodes 20-23 is to be used for all or at least for very many imaging regions 10, for which reason the other additional electrode forms described can also be suitable.

The semiconductor detector shown in FIG. 3 has four quadrants and/or subregions 34-36 in each of which four imaging regions 10 are arranged and which each have at least one of the additional electrodes 16-23. If a separate acquisition of second measurement values takes place for each of the additional electrodes 16-23 via a respectively associated current sensor, the properties of the semiconductor detector, for example, its temperature or existing defects and/or their effects on the measurement can thus be taken into account separately for the individual quadrants, since a spatially resolved acquisition of the second measurement values can take place. By this, local effects can also be compensated for, for example, in that a locally different heating of the semiconductor detector takes place and/or in that, in different regions, different dark current corrections are used if the second measurement values for the different subregions 34-37 indicate different properties and/or states of the semiconductor material.

Although the invention has been illustrated and described in detail by way of the preferred exemplary embodiment, the invention is not restricted by the examples disclosed and other variations can be derived herefrom by a person skilled in the art without departing from the protective scope of the invention.

The invention claimed is:

1. An X-ray imager comprising:
an X-ray source;
a semiconductor detector; and
a processor,
wherein on a rear side of the semiconductor detector facing away from a front side, in each of a plurality of imaging regions of the semiconductor detector, at least one imaging electrode is arranged and a plurality of imaging detectors each contact at least one of the imaging electrodes to acquire first measurement values relating to X-ray signals of the imaging electrodes,
wherein the processor is configured to establish an image dataset dependent upon the first measurement values,
wherein at least one additional electrode is arranged on the rear side of the semiconductor detector outside the imaging regions, at least one current sensor contacts the at least one additional electrode to acquire current flow by way of second measurement values relating to the at least one additional electrode,
wherein the imaging electrodes and the at least one additional electrode are each connected by way of at least one respective contact to a respective connecting electrode of an integrated circuit which implements the imaging detector, and
wherein the at least one additional electrode is connected, via at least two contacts spaced apart from one another, to one or each to one of the connecting electrodes of the integrated circuit.

2. The X-ray imager as claimed in claim 1, wherein the processor is configured to control at least one component of the X-ray imager dependent upon the second measurement values.

3. The X-ray imager as claimed in claim 2, wherein the processor is configured to control a heater for heating the semiconductor detector as the component dependent upon the second measurement values.

4. The X-ray imager as claimed in claim 3, wherein the processor is configured to establish the image dataset additionally dependent upon the second measurement values.

5. The X-ray imager as claimed in claim 1, further comprising an anti-scatter grid arranged between the X-ray source and the front side of the semiconductor detector facing toward the X-ray source, wherein at least one shading region of the semiconductor detector is screened from the X-ray source by an X-ray absorbent material of the anti-scatter grid, wherein in each case, the at least one additional electrode is arranged at least partially in the at least one shading region.

6. The X-ray imager as claimed in claim 1, wherein the integrated circuit additionally implements the current sensor.

7. The X-ray imager as claimed in claim 1, wherein the current sensor is configured separately from the integrated circuit, wherein the integrated circuit has a circuit portion which serves to feed current to be measured from each additional electrode to the respective current sensor.

8. The X-ray imager as claimed in claim 1, wherein in each case, at least one of the additional electrodes is designed as a straight strip, as a strip surrounding an imaging region, and/or is cruciform.

9. The X-ray imager as claimed in claim 1, wherein the at least one additional electrode and the imaging electrodes are electrically connected to one another or to a common reference potential such that a potential on the imaging electrodes and the potential on the at least one additional electrode differ from one another during operation of the X-ray facility by not more than 1 Volt or not more than 200 mV.

10. The X-ray imager as claimed in claim 1, wherein a plurality of contiguous subregions of the semiconductor detector, each of which comprises at least one of the imaging electrodes, are each associated with at least one of the current sensors which contacts at least one of the additional electrodes arranged in this subregion, to acquire the current flow by way of the second measurement values relating to this additional electrode.

11. A method for operating an X-ray scanner which comprises an X-ray source and a semiconductor detector, the method comprising:
acquiring first measurement values relating to X-ray signals of imaging electrodes, the imaging electrodes being on a rear side of the semiconductor detector facing away from a front side, wherein at least one imaging electrode is arranged in each of a plurality of imaging regions of the semiconductor detector which lie outside of the shading region;
acquiring second measurement values relating to current flow through at least one additional electrode, wherein the at least one additional electrode is arranged on the rear side of the semiconductor detector outside the imaging regions, wherein the at least one additional electrode comprises isolated strips positioned between different pairs of the imaging regions; and
establishing an image dataset dependent upon the first measurement values.

12. The method of claim 11, wherein establishing comprises establishing the image dataset dependent also on the second measurement values.

13. The method of claim 12, wherein the image data set is dependent on the second measurement values through correction of the first measurement values based on the second measurement values.

14. The method of claim 11, further comprising controlling a heater based on the second measurement values.

15. The method of claim 11, wherein acquiring the second measurement values comprises acquiring from the shaded region shaded by an anti-scatter grid.

16. The method of claim 11, wherein acquiring the second measurement values comprises measuring with each of the at least one additional electrode connected via at least two contacts spaced apart from one another to corresponding electrodes of an integrated circuit.

17. An X-ray imager comprising:
an X-ray source;
a semiconductor detector; and
a processor,
wherein on a rear side of the semiconductor detector facing away from a front side, in each of a plurality of imaging regions of the semiconductor detector, at least one imaging electrode is arranged and a plurality of imaging detectors each contact at least one of the imaging electrodes to acquire first measurement values relating to X-ray signals of the imaging electrodes,
wherein the processor is configured to establish an image dataset dependent upon the first measurement values,
wherein at least one additional electrode is arranged on the rear side of the semiconductor detector outside the imaging regions, at least one current sensor contacts the at least one additional electrode to acquire current flow by way of second measurement values relating to the at least one additional electrode,
wherein the imaging electrodes and the at least one additional electrode are each connected by way of at least one respective contact to a respective connecting electrode of an integrated circuit which implements the imaging detector, and
wherein the current sensor is configured separately from the integrated circuit, wherein the integrated circuit has a circuit portion which serves to feed current to be measured from each additional electrode to the respective current sensor.

* * * * *